(12) United States Patent
Reynolds

(10) Patent No.: US 9,224,508 B2
(45) Date of Patent: Dec. 29, 2015

(54) RADIATION RESISTANT MEDICAL GOWN

(71) Applicant: Ann Reynolds, Palmetto, FL (US)

(72) Inventor: Ann Reynolds, Palmetto, FL (US)

(*) Notice: Subject to any disclaimer, the term of this patent is extended or adjusted under 35 U.S.C. 154(b) by 0 days.

(21) Appl. No.: 14/278,381

(22) Filed: May 15, 2014

(65) Prior Publication Data

US 2014/0367594 A1    Dec. 18, 2014

Related U.S. Application Data

(60) Provisional application No. 61/823,446, filed on May 15, 2013.

(51) Int. Cl.
| | | |
|---|---|---|
| *G21F 3/025* | (2006.01) | |
| *A61B 6/10* | (2006.01) | |
| *A41B 3/02* | (2006.01) | |
| *A41D 13/12* | (2006.01) | |

(52) U.S. Cl.
CPC . *G21F 3/025* (2013.01); *A41B 3/02* (2013.01); *A41D 13/1209* (2013.01); *A61B 6/107* (2013.01); *A41D 2400/00* (2013.01); *A41D 2400/52* (2013.01); *A41D 2600/00* (2013.01)

(58) Field of Classification Search
USPC ........... 250/505.1, 515.1, 516.1, 518.1, 519.1
See application file for complete search history.

(56) References Cited

U.S. PATENT DOCUMENTS

| | | | |
|---|---|---|---|
| 4,196,355 A | 4/1980 | Maine | |
| 8,624,212 B2 | 1/2014 | Yang et al. | |
| 2005/0191918 A1* | 9/2005 | Langley et al. | 442/59 |
| 2010/0107320 A1* | 5/2010 | Rees | A61B 6/107 2/456 |

* cited by examiner

*Primary Examiner* — Nicole Ippolito
(74) *Attorney, Agent, or Firm* — GrayRobinson, P.A.; Michael J. Colitz, III

(57) ABSTRACT

Disclosed is a radiation resistant medical gown. More specifically, the invention relates to a medical gown that incorporates a radiation resistant and/or dissipating material into select portions of the garment. The gown further includes an upstanding collar that protects the wearer's thyroid from radiation exposure. The collar includes a Velcro® type fastener that prevents the collar from sagging. The gown is both sterile and disposable.

16 Claims, 4 Drawing Sheets

RADIATION RESISTANT MEDICAL GOWN

RELATED APPLICATION DATA

This application claims priority to application Ser. No. 61/823,446 filed on May 15, 2013, and entitled "Radiation Resistant Medical Gown." The contents of this application are fully incorporated herein for all purposes.

TECHNICAL FIELD

This disclosure relates to a medical gown. More particularly, the present disclosure relates to a disposable medical gown that is radiation resistant.

BACKGROUND OF THE INVENTION

Radiation shields are commonly used by medical personnel. These shields are worn by both medical personnel and patients when radiation is being applied. For example, patients are often exposed to radiation during x-rays. Various types of radiation treatments are also applied during cancer treatments. Regardless of the use, it is important that the radiation exposure to both the patient and the health care worker be minimized. For this reason, lead aprons are usually worn by the patient and/or the healthcare worker.

The problem with such "x-ray aprons" is that they are designed to be reused. Thus, in order for x-ray aprons to be used in sterile environments, such as operating rooms, they must be covered with a sterile fabric gown. However, even with such a covering, blood and other drainage often strikes through to contaminate the underlying shield. Moreover, traditional x-ray aprons tend to be heavy and bulky and thereby restrict the movements of the wearer.

For example, U.S. Pat. No. 4,196,355 to Maine (the '355 Patent) discloses a two-piece radiation shield vest and skirt for protecting a wearer's upper and lower body, respectively, from radiation. The vest and skirt disclosed in the '355 Patent, however, fails to protect a wearer's neck, thereby leaving the thyroid gland exposed to the harmful effects of ionizing radiation. Further, the vest and skirt are reusable and thus may result in the undesirable transfer of germs or other contaminants from one user to another if not properly sterilized. Further, the vest and skirt of the '355 Patent is heavy and bulky and requires adjustability for distributing the weight and minimizing fatigue.

Also known in the art is U.S. Pat. No. 8,624,212 to Yang, et al. (the '212 Patent), which discloses radiation resistant clothing consisting of a first radiation resistant layer for reflecting electromagnetic radiation and a second radiation resistant layer for absorbing electromagnetic radiation. The clothing disclosed in the '212 application, however, also fails to protect the neck of the user, thereby leaving the thyroid gland susceptible to the harmful effects of radiation. Further, the garments of neither the '355 Patent or the '212 Patent are single-use, sterile, or disposable.

What is needed, therefore, is a sterile, single use, light weight surgical gown that is radiation resistant and that protects the patient's and/or health care worker's neck and lower body from unwanted radiation exposure. The radiation resistant gown of the present disclosure fulfills these and other needs in the art.

SUMMARY OF THE INVENTION

This disclosure provides a medical gown that is radiation resistant.

The disclosed system has several important advantages. For example, the radiation resistant gown of the present disclosure is disposable and designed for single use.

A further possible advantage is achieved by providing a radiation resistant medical gown with a thyroid collar for protecting the wearer's thyroid from radiation exposure.

Still yet another possible advantage of the present system is to provide a radiation resistant gown that employs a radiation dissipating polymer material underneath of a sterile fabric.

Another advantage of the present system is achieved by providing a gown where a radiation resistant or dissipating material is formed into select portions of the garment.

Various embodiments of the invention may have none, some, or all of these advantages. Other technical advantages of the present invention will be readily apparent to one skilled in the art.

BRIEF DESCRIPTION OF THE DRAWINGS

For a more complete understanding of the present disclosure and its advantages, reference is now made to the following descriptions, taken in conjunction with the accompanying drawings, in which.

Similar reference characters refer to similar parts throughout the several views of the figures.

DETAILED DESCRIPTION OF THE DRAWINGS

The present invention relates to a radiation resistant medical gown. More specifically, the invention relates to a medical gown that incorporates a radiation resistant and/or dissipating material into select portions of the garment. The gown further includes an upstanding collar that protects the wearer's thyroid from radiation exposure. In one embodiment, the collar includes a Velcro® type fastener that prevents the collar from sagging. The gown is both sterile and disposable. The various components of the present invention, and the manner in which they interrelate, are described in greater detail hereinafter.

Figure 1:
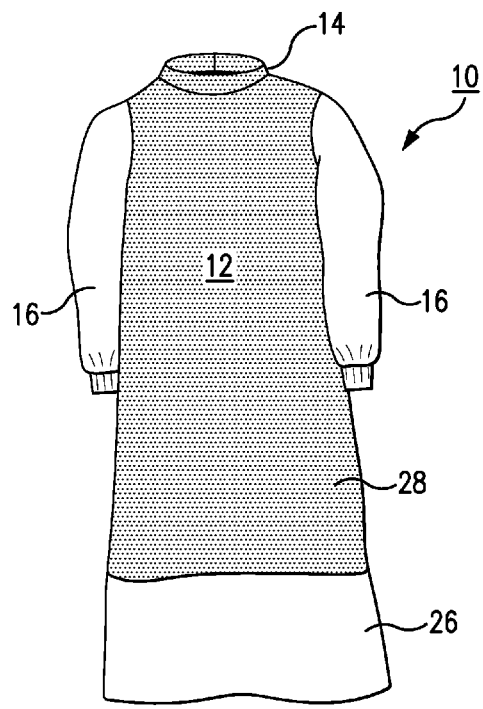
FIG. 1 is a front view of the radiation resistant gown of the present invention.
Figure 2:
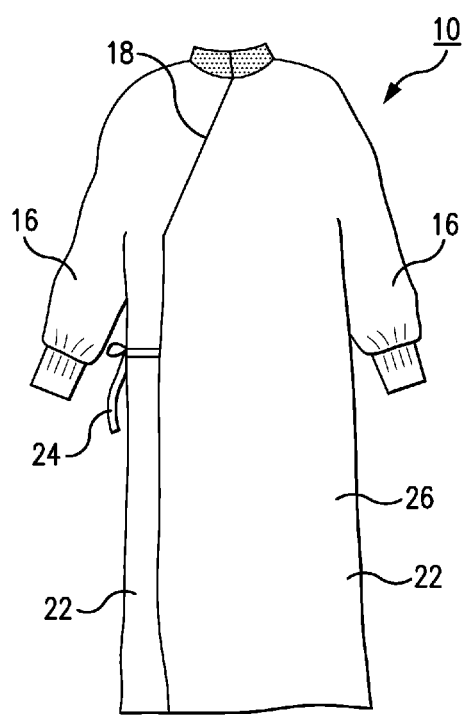
FIG. 2 is a rear view of the radiation resistant gown of the present invention.

With reference now to FIGS. 1 and 2, an embodiment of the gown 10 of the present disclosure is depicted. The gown 10 includes a chest area 12, a neck opening 14, and sleeves 16. Gown 10 is opened in the back 18. The opposing sides 22 are designed to be brought together at the back 18 and secured via a strap 24. Strap 24 is located about the waist of the wearer. The outer layer of the gown is made from a sterile fabric 26.

In one embodiment, a radiation resistant material 28 is sewn to the fabric in the chest area 12 of the gown 10. In the preferred embodiment, the radiation resistant material 28 is secured to the inner surface of fabric layer 26. However, it is also within the scope of the invention to secure radiation resistant material 28 over top of fabric layer 26. In either event, the layers can be joined by sewing the periphery of the radiation resistant material 28 to the inside or the outside of fabric layer 26. Alternatively, heat sealing can be employed in lieu of sewing. Radiation resistant material 28 should extend about neck opening 14. Radiation resistant material 28 should likewise extent down below the reproductive organs of the wearer. Notably, the radiation resistant material 28 need not extent to the bottom of garment 10. Nor does the radiation resistant material 28 need to extend along sleeves 16. Nonetheless, it is within the scope of the present invention to include the material in these areas.

Any of a variety of radiation resistant materials can be used in connection with the present invention. However, in a preferred but non-limiting embodiment, the radiation resistant material is an organic polymer, such as a polypropylene material. The material described in U.S. Pat. No. 7,655,723 to Musgrave may suffice in this regard. The '723 Patent is incorporated herein by reference. The material may either deflect, absorb, dissipate and/or neutralize the radiation as needed. Ideally, the radiation resistant material is formed from a lightweight polymer based material.

Figure 3:
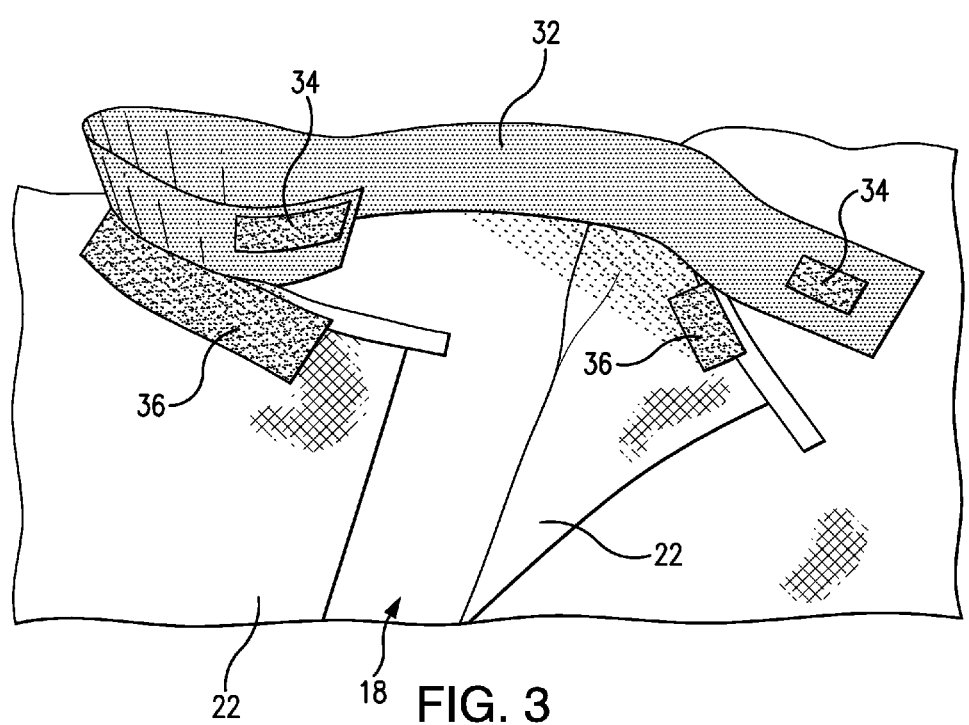
FIG. 3 is a detailed view of the collar in the opened orientation.
Figure 4:
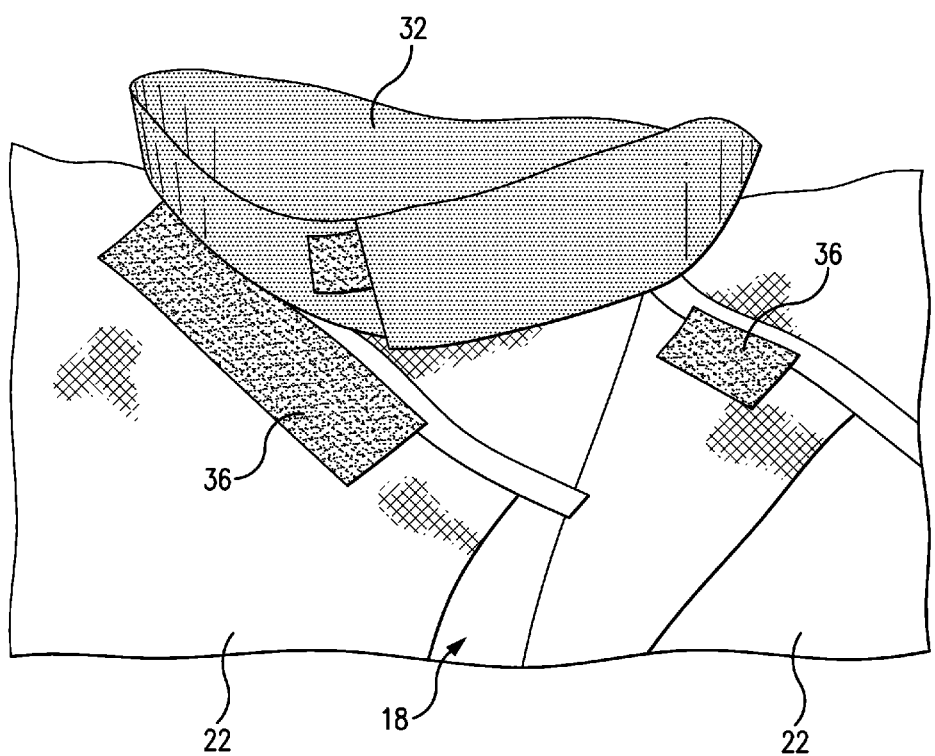
FIG. 4 is a detailed view of the collar in the partially opened orientation.
Figure 5:
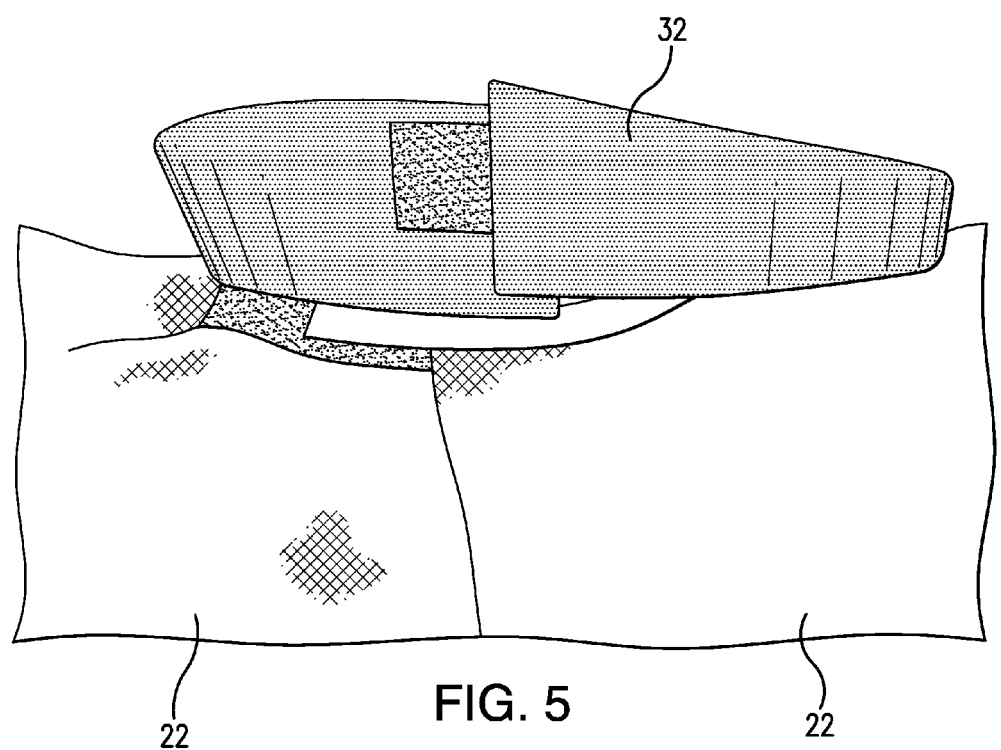
FIG. 5 is a detailed view of the collar in the closed orientation.

As depicted in FIGS. 3-5, an embodiment of the gown 10 of the present disclosure further includes a thyroid collar 32 that stands up to protect the neck region of the wearer. Thyroid collar 32 can be formed from the same materials as the chest area 12 of gown 10. Alternatively, collar 32 can be formed entirely of the above described radiation resistant polymer material. To ensure that collar 32 stands up and is not prone to drooping, twin fasteners are included at the back of the wearer's neck. Namely, the ends of the thyroid collar 32 are free and each includes a hook and pile fastener 34, such as a Velcro® type fastener. Although the majority of collar 32 is attached to the upper extent of the gown, the distal ends of the collar 32 are detached and free. These ends can be joined in an overlapping configuration and secured with Velcro® fasteners 34. The opposing sides of the gown 22 likewise include hook and pile fasteners 36 at their upper extents. Thus, in order to close gown 10, the two opposite ends 22 are brought together in overlapping fashion at the wearer's back. Tie strap 24 can be used to keep the two ends 22 together. Thereafter, the Velcro® fasteners 36 at the top of gown 10 are secured. Next, the two ends of the thyroid collar 32 are brought together such that the collar fits securely about the wearer's neck. The ends of the thyroid collar 32 are then similarly secured via the Velcro® fasteners 34 at the ends of collar 32. It has been found that this arrangement keep the collar 32 propped up during use and ensure that the lower neck region (including the thyroid) are adequately shielded from radiation.

Although this disclosure has been described in terms of certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure.

What is claimed is:

1. A radiation resistant gown for protecting a wearer from radiation, the gown comprising:
    a body portion having an outer layer and an inner layer, the outer layer being formed from a flexible sterile fabric material and the inner layer being formed from a radiation resistant material, the body portion defining a chest area, a neck opening, and a pair of sleeves, the outer layer having an outer surface and an inner surface, the inner layer secured to the inner surface of the outer layer; and
    a collar formed from an outer flexible sterile fabric layer and an inner layer of a radiation resistant material, the collar being secured to the body portion and upstanding from the neck opening, the collar having a pair of distal ends, each distal end including hook and pile fasteners that are adopted to releasably engage one another,
    wherein the radiation resistant material of the body portion and collar are operable for at least one of dissipating, absorbing, neutralizing, and deflecting radiation.

2. The radiation resistant gown as described in claim 1, wherein the body portion further comprises opposing sides that are brought together at the wearer's back.

3. The radiation resistant gown as described in claim 2, wherein the opposing sides are secured to each other via a pair of fasteners and a strap.

4. The radiation resistant gown as described in claim 3, wherein the strap is located about the wearer's waist.

5. The radiation resistant gown as described in claim 1, wherein a periphery of the inner layer is sewn to the inner surface of the outer layer.

6. The radiation resistant gown as described in claim 1, wherein a periphery of the inner layer is heat sealed to the inner surface of the outer layer.

7. The radiation resistant gown as described in claim 1, wherein the at least one radiation resistant material protects the wearer's reproductive organs.

8. The radiation resistant gown as described in claim 1, wherein the at least one radiation resistant material of the collar protects a wearer's thyroid.

9. The radiation resistant gown as described in claim 1, wherein the pair of distal ends are brought together behind a wearer's neck.

10. The radiation resistant gown as described in claim 1, wherein the at least one radiation resistant material comprises polypropylene.

11. The radiation resistant gown as described in claim 1, wherein the outer layer comprises a sterile fabric.

12. The radiation resistant gown as described in claim 1, wherein the at least one radiation resistant material of the inner layer is limited to the chest area.

13. A radiation resistant garment for protecting a wearer from radiation, the garment comprising:
    an outer sterile flexible fabric layer and an inner radiation resistant layer, each layer having an upper extent and a lower extent and defining a chest area and a neck opening, the outer layer having an outer surface and an inner surface, the inner layer secured to the inner surface of the outer layer,
    a collar formed from an outer sterile flexible fabric layer and an inner layer of a radiation resistant material, the collar being secured to the garment and upstanding from the neck opening.

14. The radiation resistant garment as described in claim 13, wherein the radiation resistant material comprises an organic polymer.

15. The radiation resistant garment as described in claim 14, wherein the organic polymer comprises polypropylene.

16. The radiation resistant garment as described in claim 13 further comprising a pair of sleeves extending from the chest area.

* * * * *